United States Patent [19]

Wilk

[11] Patent Number: 5,338,308
[45] Date of Patent: Aug. 16, 1994

[54] METHOD AND APPARATUS FOR INHIBITING CATHETER SEPSIS

[76] Inventor: Peter J. Wilk, 185 W. End Ave., New York, N.Y. 10023

[21] Appl. No.: 85,748

[22] Filed: Jun. 30, 1993

[51] Int. Cl.⁵ .............................................. A61M 25/02
[52] U.S. Cl. ........................... 604/180; 128/DIG. 26; 604/43; 604/280
[58] Field of Search ............... 604/174, 179, 180, 280, 604/284, 43; 128/DIG. 26

[56] References Cited

U.S. PATENT DOCUMENTS

| | | | |
|---|---|---|---|
| 4,275,721 | 6/1981 | Olson | 604/180 |
| 4,380,234 | 4/1983 | Kamen | 604/180 |
| 4,547,187 | 10/1985 | Kelly | 604/284 |
| 4,666,426 | 5/1987 | Aigner | 604/43 |
| 4,842,582 | 6/1989 | Mahurkar | 604/280 |
| 4,886,507 | 12/1989 | Patton et al. | 604/284 |
| 4,897,079 | 1/1990 | Zaleski et al. | 604/43 |
| 5,053,004 | 10/1991 | Markel et al. | 604/43 |
| 5,057,073 | 10/1991 | Martin | 604/280 |
| 5,087,245 | 2/1992 | Doan | 128/DIG. 12 |
| 5,108,366 | 4/1992 | Schatz | 604/280 |
| 5,201,725 | 4/1993 | Kling | 604/284 |
| 5,242,432 | 9/1993 | DeFrank | 604/284 |

*Primary Examiner*—Paul J. Hirsch
*Attorney, Agent, or Firm*—R. Neil Sudol; Henry D. Coleman

[57] ABSTRACT

An assembly for inhibiting catheter sepsis comprises an intravenous catheter inserted through a skin surface at an insertion point, a patch attached to the skin surface about the insertion point so as to cover a region of the skin surface and a segment of the catheter at the skin surface, and an ancillary tube having a distal end portion disposed between the patch and the skin surface upon an application of the patch to the skin surface. In the distal end portion, the ancillary tube has an outlet port which is located between the patch and the skin surface upon application of the patch to the skin surface. The ancillary tube has an inlet port spaced in a proximal direction from the outlet port so that the inlet port is accessible via a needle upon application of the patch to the skin surface.

21 Claims, 2 Drawing Sheets

METHOD AND APPARATUS FOR INHIBITING CATHETER SEPSIS

BACKGROUND OF THE INVENTION

This invention relates to a method for inhibiting catheter sepsis. This invention also relates to an associated apparatus for inhibiting catheter sepsis.

One of the most common problems in hospitals is the incidence of infection at the insertion points of catheters, for example, catheters used for intravenous access. Because of the likelihood and danger of infection, hospitals have teams of nurses whose sole responsibility is the maintenance of catheter insertion sites on the patients. The teams periodic check and cleanse the long-term indwelling catheters and reinsert the catheters, if necessary. Sometimes a catheter must be moved to a different site on the patient. In some cases, however, obtaining venous access is difficult, e.g., where the venous pressure is far below normal. In such cases, once venous access is obtained, it is important, if not imperative, to maintain access at the same point. The dangers of catheter sepsis clearly militate against such access maintenance.

Phlebitis is infection of a vein at an intravenous catheter insertion site. One problem with phlebitis is an associated rise in temperature of the patient. Confusion arises as to whether the temperature rise is due to a lung infection (pneumonia) or to phlebitis.

Catheter sepsis can lead to a life threatening condition, for example, septic thrombo phlebitis.

OBJECTS OF THE INVENTION

An object of the present invention is to provide a method for reducing the incidence and/or severity of catheter sepsis.

A further object of the present invention is to provide a method for facilitating the maintenance of uninfected conditions at catheter insertion sites.

Another object of the present invention is to provide such a method which reduces the necessity for periodic checking of catheter insertion sites by hospital personnel.

A further object of the present invention is to provide an apparatus or assembly for reducing the incidence and/or severity of catheter sepsis, for facilitating the maintenance of uninfected conditions at catheter insertion sites, and/or for reducing the necessity for periodic checking of catheter insertion sites by hospital personnel.

These and other objects of the present invention will be apparent from the drawings and detailed descriptions herein.

SUMMARY OF THE INVENTION

An assembly for inhibiting catheter sepsis comprises, in accordance with the present invention, an intravenous catheter insertable through a skin surface at an insertion point, a patch attachable to the skin surface about the insertion point so as to cover a region of the skin surface and a segment of the catheter at the skin surface, and an ancillary tube having a distal end portion disposed between the patch and the skin surface upon an application of the patch to the skin surface. In the distal end portion, the ancillary tube has an outlet port which is located between the patch and the skin surface upon application of the patch to the skin surface. The ancillary tube has an inlet port spaced in a proximal direction from the outlet port so that the inlet port is accessible via a needle upon application of the patch to the skin surface.

In a specific embodiment of the invention, the ancillary tube is attached to the catheter. The ancillary tube may define a channel which extends parallel to the catheter lumen. More particularly, the ancillary tube may surround the catheter to define a cylindrical channel about the catheter. In that event, the ancillary tube may include an inlet branch extending away from the catheter, the inlet port being disposed in the inlet branch.

According to another feature of the present invention, the catheter assembly further comprises a flange projecting from the ancillary tube and the catheter to form an arrest to further insertion of the catheter into a patient. The output port is then preferably disposed proximately to the flange.

According to an additional feature of the present invention, the catheter assembly further comprising a valve in the ancillary tube. The valve may, for example, take the form of a self-sealing membrane.

According to another feature of the present invention, the catheter assembly further comprises a dispensing mechanism connected to the ancillary tube for injecting an antimicrobial agent through the inlet port and the ancillary tube so that the antimicrobial agent is ejected from the outlet port onto the skin surface. The dispensing mechanism may include means for automatically injecting the antimicrobial agent through the inlet port and the ancillary tube. The automatic injection is implemented under the control of or in response to a signal generated by a timer which is operatively connected to the dispensing mechanism for timing the dispensing of the antimicrobial agent.

It is to be noted that the ancillary tube may be separate from the catheter, connected to the catheter by the patch upon application thereof to the skin surface of the patient.

A method for inhibiting catheter sepsis comprises, in accordance with the present invention, the steps of (a) providing an intravenous catheter, an ancillary tube and a patch, the ancillary tube having an inlet port and an outlet port, (b) inserting the catheter through a skin surface of a patient into a blood vessel of the patient at a catheter insertion point, (c) disposing the ancillary tube so that the outlet port is substantially juxtaposed to the skin surface and the insertion point, (d) applying the patch over the catheter and the ancillary tube about the insertion point, and (e) injecting an antimicrobial agent through the inlet port and the ancillary tube so that the antimicrobial agent is ejected from the outlet port onto the skin surface beneath the patch.

Where the ancillary tube is attached to the catheter, the disposition of the ancillary tube so that the outlet port is substantially juxtaposed to the skin surface and the insertion point includes the step of inserting the catheter into the patient so that the outlet port remains outside the patient.

Where the catheter and the ancillary tube are provided with a flange projecting from the catheter and the ancillary tube, the disposition of the ancillary tube includes the step of inserting the catheter and the ancillary tube into the patient until the flange abuts the skin surface.

Where a valve is provided in the ancillary tube, the method further comprises the steps of opening the valve prior to the step of injecting and closing the valve after the step of injecting. Where the valve is a self-sealing membrane, the step of opening the valve includes the step of forming a perforation in the membrane, while the step of closing includes the step of closing the perforation.

According to further features of the present invention, the step of injecting the antimicrobial agent is performed automatically upon timing of a predetermined interval since a prior application of the antimicrobial agent.

A method and apparatus in accordance with the present invention reduces the incidence and/or severity of catheter sepsis in part by facilitating the maintenance of uninfected conditions at catheter insertion sites. A method and apparatus in accordance with the present invention can reduce the necessity for periodic checking of catheter insertion sites by hospital personnel.

DETAILED DESCRIPTION

Figure 1:
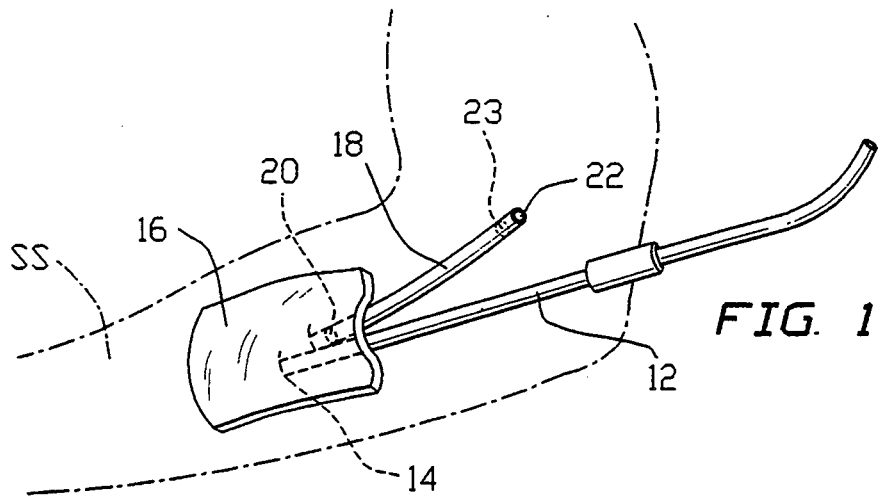
FIG. 1 is a schematic perspective view of an assembly for inhibiting catheter sepsis, in accordance with the present invention, showing the placement of the assembly on the arm of a patient.

As illustrated in FIG. 1, an assembly for inhibiting catheter sepsis comprises an intravenous catheter 12 insertable through a skin surface SS of a patient at an insertion point 14. A patch 16 is attachable to the patient's skin surface about insertion point 14 so as to cover a region of the skin surface and a segment of catheter 12 at skin surface SS. An ancillary tube 18 has a distal end portion disposed between patch 16 and skin surface SS upon an application of the patch to the skin surface. In the distal end portion, ancillary tube 18 has an outlet port 20 which is located between patch 16 and skin surface SS upon application of the patch to the skin surface. Ancillary tube 18 has an inlet port 22 spaced in a proximal direction from outlet port 20 so that the inlet port is accessible via a needle upon application of patch 16 to skin surface SS.

Ancillary tube 18 is provided at a proximal end, i.e., primately to inlet port 22, with a valve 23 which may take the particular form of a self-sealing membrane. Accordingly, upon installation of the catheter assembly to skin surface SS, as illustrated in FIG. 1, a hypodermic needle (not shown) may be inserted into ancillary tube 18 via inlet port 22 and membrane valve 23. A syringe (not shown) is then actuated to inject an antiseptic agent such as Betadyne into ancillary tube 18. The ancillary tube conducts or guides the antiseptic to skin surface SS. The antiseptic is dispensed via outlet port 20 onto the skin surface SS about insertion point 14.

Figure 2:
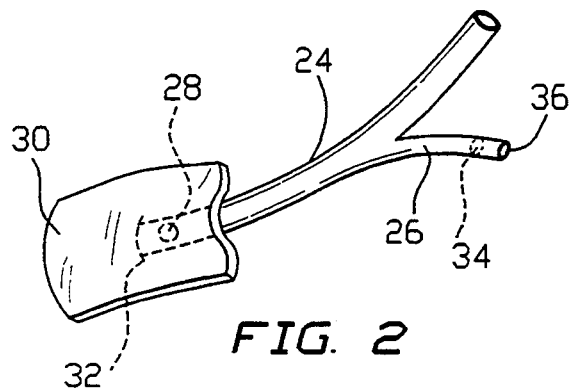
FIG. 2 is a schematic perspective view of another assembly for inhibiting catheter sepsis, in accordance with the present invention.

As illustrated in FIG. 2, another assembly for inhibiting catheter sepsis comprises a catheter 24 with an integral ancillary tube 26. Ancillary tube 26 has an outlet port 28 which is located under a skin patch 30 upon application of the patch to a patient's skin such that the patch covers the catheter assembly at an insertion point 32. Ancillary tube 26 defines a channel which is separate from the lumen of catheter 24. A self-sealing membrane valve 34 is disposed in ancillary tube 26 proximately to an inlet port 36 thereof. The sepsis-inhibiting catheter assembly of FIG. 2 is used in essentially the same manner as the assembly of FIG. 1. An antiseptic agent such as Betadyne is periodically applied to a catheter insertion site of the patient about catheter insertion point 32, thereby maintaining the site essentially free of infection.

Figure 3:
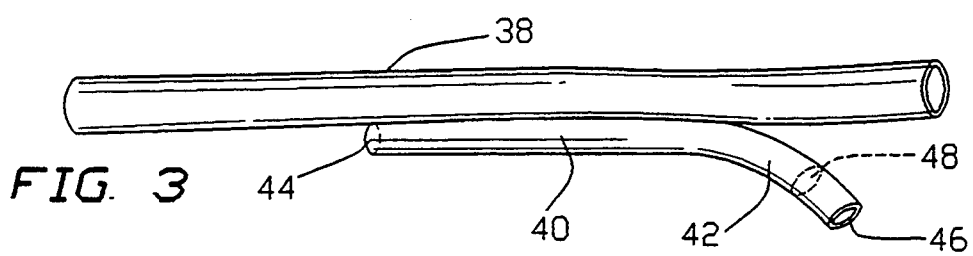
FIG. 3 is a side elevational view of a further assembly for inhibiting catheter sepsis, in accordance with the present invention.

As depicted in FIG. 3, a modified assembly for inhibiting catheter sepsis includes a catheter 38 and an ancillary tube 40. Ancillary tube 40 is attached to an outer surface of catheter 38 and extends generally parallel thereto, except for an inlet branch 42 at the promixal end of ancillary tube 40. Ancillary tube 40 has an outlet port 44 at one end and an inlet port 46 at the other end. A self-sealing membrane valve 48 is provided in inlet branch 42, near inlet port 46.

The outlet end of ancillary tube 40 (at outlet port 44) defines a shoulder which serves as an abutment or arrest to continued insertion of catheter 38 into a patient during an installation procedure. The catheter assembly of FIG. 3 may be modified by moving outlet port 44 from the tip of ancillary tube 40 to a sidewall thereof in a region about the distal end of the ancillary tube. In that event the distal end is closed for facilitating the insertion arresting function.

Figure 4:
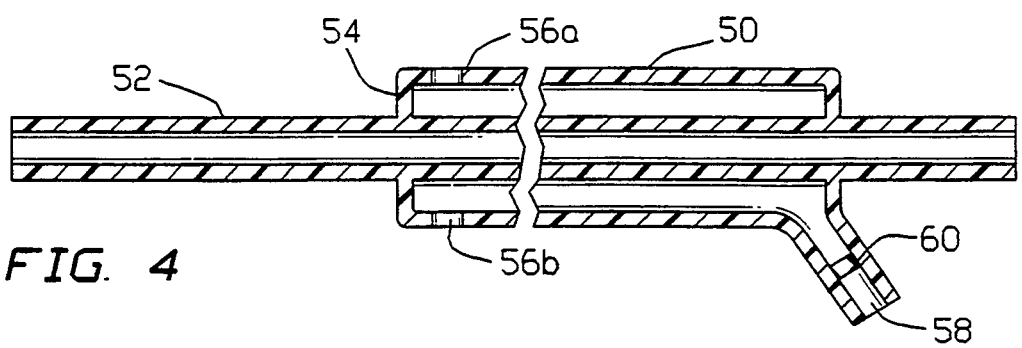
FIG. 4 is a longitudinal cross-sectional view, on a substantially enlarged scale, of an additional assembly for inhibiting catheter sepsis, in accordance with the present invention.

FIG. 4 illustrates another assembly for inhibiting catheter sepsis. A cylindrical ancillary tube 50 coaxially surrounds a catheter 52 and is closed at a distal end to define a shoulder 54 which serves as an abutment or arrest to continued insertion of catheter 52 into a patient during an installation procedure. Proximally of shoulder 54, the catheter assembly is provided with a plurality of openings or outlet ports 56a, 56b for introducing an antiseptic agent onto a skin surface at a catheter insertion site. At a proximal end, ancillary tube 50 is provided with an inlet branch or port 58 in turn provided with a self-sealing membrane valve 60. The use of the catheter assembly of FIG. 4 is the same as the utilization of the assemblies of FIGS. 2 and 3. Upon insertion of the distal end portion of catheter 52 into a patient, a hypodermic needle (not shown) is inserted into ancillary tube 50 via inlet port 58 and membrane valve 60. A syringe (not shown) injects an antiseptic agent such as Betadyne into ancillary tube 50. The antiseptic is subsequently dispensed via outlet ports 56a, 56b onto the patient's skin surface about an insertion point.

Figure 5:
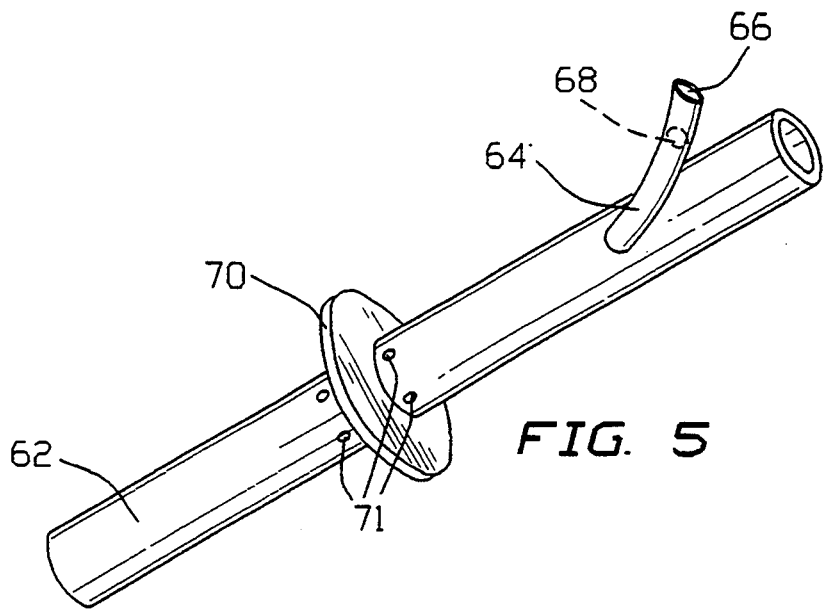
FIG. 5 is a schematic perspective view of yet another assembly for inhibiting catheter sepsis, in accordance with the present invention.

As shown in FIG. 5, yet another assembly for inhibiting catheter sepsis includes a catheter 62 with a built-in ancillary tube (not designated) having an inlet branch 64 with a port 66 and a self-sealing membrane valve 68. Catheter 62 is provided with a flange 70 which serves as an abutment or arrest to continued insertion of catheter 62 into a patient. About flange 70, catheter 62 is provided with a plurality of openings or outlet ports 71 for dispensing, onto a patient's skin surface under a cover patch (not shown), an antiseptic agent which is injected into inlet branch 64 via port 66 and self-sealing membrane valve 68.

Figure 6:
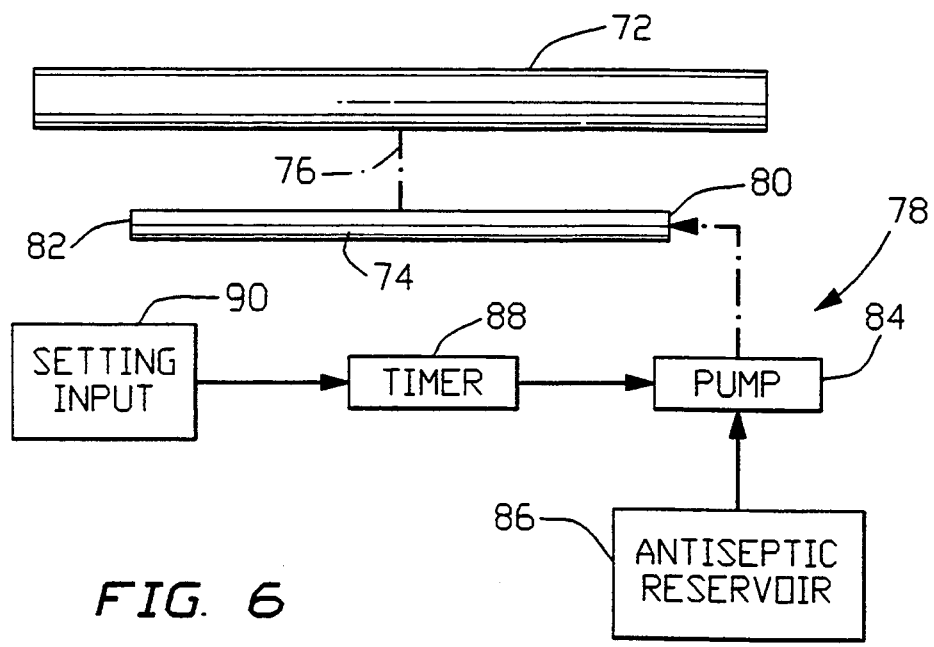
FIG. 6 is essentially a block diagram of an automatic assembly for inhibiting catheter sepsis, in accordance with the present invention.

As depicted in FIG. 6, a largely automatic assembly for inhibiting catheter sepsis includes a catheter tube 72 and an ancillary, antiseptic delivery tube 74 connected to one another, as indicated at 76. A dispensing mechanism 78 is connected to ancillary tube 74 for injecting an antimicrobial agent through an inlet port 80 and the ancillary tube so that the antimicrobial agent is ejected from an outlet port 82 onto a skin surface at a catheter insertion site. Dispensing mechanism 78 includes a pump 84 for automatically drawing the antimicrobial agent from a reservoir 86 and injecting the agent through inlet port 80 into ancillary tube 74. Pump 84 operates under the control of or in response to a signal generated by a timer 88 which is operatively connected to the dispensing mechanism for timing the dispensing of the antimicrobial agent. An input component 90 such as a numerical keyboard is connected to timer 88 for enabling the setting of different interinjection intervals to customize the dispensing mechanism 78 to particular cases.

The assembly of FIG. 6 is to be construed as a modification of any of the assemblies illustrated in FIGS. 1–5. Accordingly, any of the sepsis-reducing catheter assemblies may be made automatic or partially automatic as generally illustrated in FIG. 6. With respect to the assembly of FIG. 1, patch 16 serves as a connection 76 (FIG. 6) between the catheter and the ancillary, antiseptic-delivery tube.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An assembly for inhibiting catheter sepsis, comprising:
   an intravenous catheter insertable through a skin surface at an insertion point;
   a patch attachable to the skin surface about the insertion point so as to cover a region of said skin surface and a segment of said catheter at said skin surface; and
   an ancillary tube having a distal end portion disposed substantially between said patch and said skin surface upon an application of said patch to said skin surface, said ancillary tube having an outlet port in said distal end portion, said outlet port being located beneath said patch and proximately to said skin surface upon application of said patch to said skin surface, said ancillary tube having an inlet port spaced in a proximal direction from said outlet port so that said inlet port is accessible via a needle upon application of said patch to said skin surface.

2. The assembly defined in claim 1 wherein said ancillary tube is attached to said catheter.

3. The assembly defined in claim 2 wherein said ancillary tube surrounds said catheter to define a cylindrical channel about said catheter.

4. The assembly defined in claim 3 wherein said ancillary tube includes an inlet branch extending away from said catheter, said inlet port being disposed in said inlet branch.

5. The assembly defined in claim 2, further comprising a flange projecting from said ancillary tube and said catheter to form an arrest to further insertion of said catheter into a patient.

6. The assembly defined in claim 5 wherein said outlet port is disposed proximately to said flange.

7. The assembly defined in claim 1, further comprising a valve in said ancillary tube.

8. The assembly defined in claim 7 wherein said valve is a self-sealing membrane.

9. The assembly defined in claim 1, further comprising dispensing means connected to said ancillary tube for injecting an antimicrobial agent through said inlet port and said ancillary tube so that said antimicrobial agent is ejected from said outlet port onto said skin surface.

10. The assembly defined in claim 9 wherein said dispensing means includes means for automatically injecting said antimicrobial agent through said inlet port and said ancillary tube.

11. The assembly defined in claim 10, further comprising timing means operatively connected to said dispensing means for timing the dispensing of said antimicrobial agent.

12. The assembly defined in claim 1 wherein said patch is made of gauze.

13. The assembly defined in claim 1 wherein said ancillary tube is separate from said catheter.

14. A method for inhibiting catheter sepsis, comprising the steps of:
   providing an intravenous catheter, an ancillary tube and a patch, said ancillary tube having an inlet port and an outlet port;
   inserting said catheter through a skin surface of a patient into a blood vessel of the patient at a catheter insertion point;
   disposing said ancillary tube so that said outlet port is substantially juxtaposed to said skin surface and said insertion point;
   applying said patch over said catheter and said ancillary tube about said insertion point; and
   injecting an antimicrobial agent through said inlet port and said ancillary tube so that said antimicrobial agent is ejected from said outlet port proximately to said skin surface beneath said patch.

15. The method defined in claim 14 wherein said ancillary tube is attached to said catheter, said step of disposing including the step of inserting said catheter into the patient so that said outlet port remains outside the patient.

16. The method defined in claim 15 wherein said catheter and said ancillary tube are provided with a flange projecting from said catheter and said ancillary tube, said step of disposing including the step of inserting said catheter and said ancillary tube into the patient until said flange abuts said skin surface.

17. The method defined in claim 14 wherein a valve is provided in said ancillary tube, further comprising the steps of opening said valve prior to said step of injecting and closing said valve after said step of injecting.

18. The method defined in claim 17 wherein said valve is a self-sealing membrane, said step of opening including the step of forming a perforation in said membrane, said step of closing including the step of closing said perforation.

19. The method defined in claim 14 wherein said step of injecting is performed automatically.

20. The method defined in claim 19, further comprising the step of timing an interval between successive applications of said antimicrobial agent, said step of injecting being performed automatically upon the lapse of an interval of a predetermined duration.

21. The method defined in claim 14 wherein said ancillary tube is separate from said catheter, said step of disposing being performed separately from said step of inserting.

* * * * *